United States Patent [19]
Kapounek et al.

[11] Patent Number: 5,328,447
[45] Date of Patent: Jul. 12, 1994

[54] SPINE PROTECTOR

[75] Inventors: Frank A. Kapounek, Munster Hamlet; Christopher R. P. Withnall, Ottawa, both of Canada

[73] Assignee: Med-Eng Systems, Inc., Ottawa, Canada

[21] Appl. No.: 29,632

[22] Filed: Mar. 11, 1993

[51] Int. Cl.⁵ .............................................. A61F 5/04
[52] U.S. Cl. .......................................... 602/19; 02/92; 128/846
[58] Field of Search .................... 602/18, 19; 128/846, 128/869-870, 873-874; 2/2, 44, 92

[56] References Cited

U.S. PATENT DOCUMENTS

| | | | |
|---|---|---|---|
| 1,316,915 | 9/1919 | Meyer et al. | 602/19 |
| 2,828,737 | 4/1958 | Hale | 602/19 |
| 4,285,336 | 8/1981 | Oebser et al. | 602/19 |
| 4,516,273 | 5/1985 | Gregory et al. | 2/2 |
| 4,541,419 | 9/1985 | Osawa | 602/19 |
| 4,680,812 | 7/1987 | Weigl | 2/2 |
| 5,140,995 | 8/1992 | Uhl | 2/2 X |

FOREIGN PATENT DOCUMENTS

| | | |
|---|---|---|
| 550539 | 12/1957 | Canada . |
| 909101 | 9/1972 | Canada . |
| 930270 | 7/1973 | Canada . |
| 1195572 | 10/1985 | Canada . |
| 1212202 | 10/1986 | Canada . |
| 2030710 | 5/1991 | Canada . |
| 2029300 | 12/1991 | Canada . |
| 2002800 | 11/1992 | Canada . |

Primary Examiner—Richard J. Apley
Assistant Examiner—Linda C. M. Dvorak
Attorney, Agent, or Firm—Evenson, McKeown, Edwards & Lenahan

[57] ABSTRACT

Disclosed is a unique spine protector for use with or without protective clothing and in particular, in bomb disposal suits or in sports related activities. The protector is made up of a plurality of overlapping elongate support members having a central recess in the mid-portion thereof such that when an external force is applied to the spine protector, the force exerted is transmitted to the spinal muscles and/or thoracic support structures on either side of the vertebrae while the vertebrae remain minimally loaded. The spine protector is made up of two sizes of support members which overlap each other in mating relationship and are loosely joined so that the spine protector can flex in three dimensions.

11 Claims, 5 Drawing Sheets

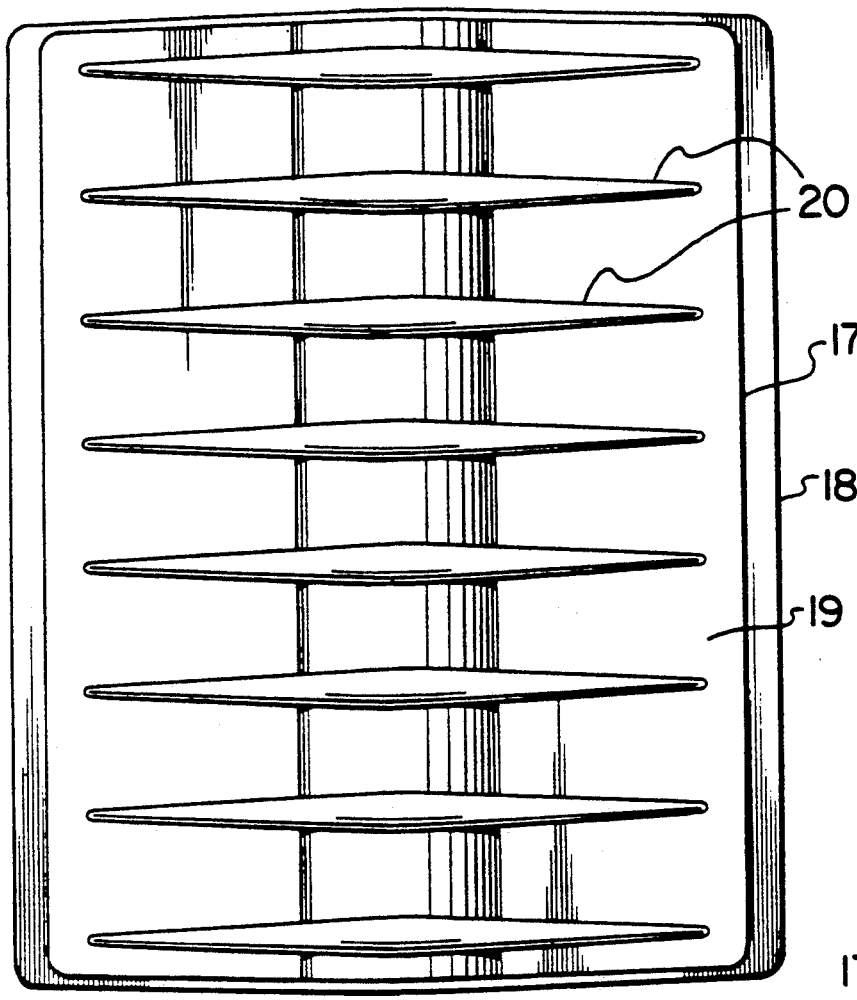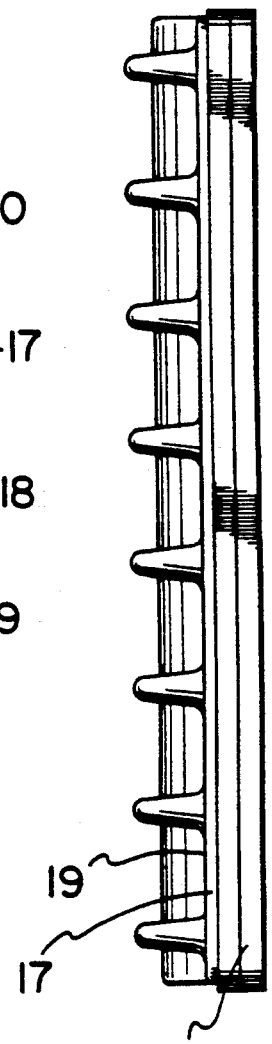
FIG. 7A
FIG. 7B
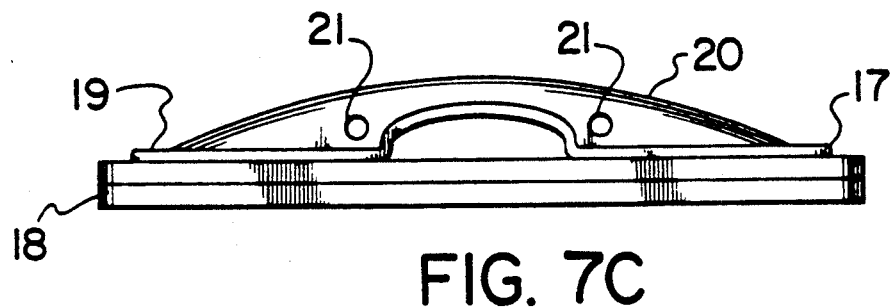
FIG. 7C

SPINE PROTECTOR

FIELD OF THE INVENTION

This invention is related to a spine protector, more particularly a spine protector adapted to fit into a seam or pocket in protective clothing suit or in a pouch mounted below existing shoulder and/or chest armour used in sports related activities or as a stand-alone in a harness.

BACKGROUND OF THE INVENTION

Protective clothing, particularly designed for protection of the spine, is well known. All of the devices known today suffer from two principal problems: (1) there is not sufficient flexibility in the protective gear; and (2) the known spine protectors bear directly upon the vertebrae. Thus, an external force is transmitted directly to the vertebrae in spite of the use of large amounts of padding and other materials.

It is, therefore, an object of the present invention to provide a spine protector which is both strong and flexible and of relatively light weight.

It is a further object of the present invention to provide a spine protector which when hit with an external force, such as when a bomb technician is thrown back after an explosion onto or against objects close to them, or when an athlete impacts an unyielding object or is impacted by another athlete or an object carried by another athlete, the force is transmitted to the spinal structures on either side of the spinal column rather than to the vertebrae.

SUMMARY OF THE INVENTION

Therefore, this invention seeks to provide a flexible spine protector for use with protective clothing comprising: a plurality of elongate substantially rectangular rigid support members and a plurality of resilient elongate substantially elongate rectangular underpads; said underpads and support members being adapted, in operation, to lie perpendicular to the longitudinal axis of the spine; said support members being connected to one another in mating overlapping relationship by a fastening means; and said support members further including a concave central recess on the underside thereof; said recess being adapted to lie directly over the vertebrae of the wearer, when in use.

In a preferred embodiment of the invention, the spine protector is comprised of a number of elongate substantially rectangular support members which have generally planar bottoms and curvilinear ribbed tops. The mid-portion of the underside of each support member is recessed in a concave manner. The support members are overlapped throughout the length of the spine protector to provide complete protection.

The support members are of two types, one with wider, longer curvilinear upwardly projecting ribs, and the second with narrower and shorter upwardly projecting ribs. The upper members are adapted to overlap the lower members such that each upper member with its two curvilinear ribs overlaps one rib each of two adjacent lower members. Thus, both the upper support members and the lower support members are spaced apart from adjacent members of the same kind.

The lower members are mounted upon resilient underpads composed of a lamination of several materials. The density, thickness, contour and number of layers would be determined by the amount of protection and energy absorption desired, depending on the application. The layer which is in direct contact with the wearer can be more resilient than that which is in contact with the support members. This provides for comfort when in use while still maximizing the energy absorption during higher energy impacts.

The support members are coupled together by means of fasteners which pass through the ribs of the upper and lower members. The fasteners are loosely fastened to allow flexure of the individual components; thus, the entire spine protector can flex in three dimensions. This makes the invention more versatile for the wearer and permits it to fit the wearer's back more intimately.

In a preferred embodiment, for maximum coverage, the spine protector is about 0.76 to 0.91 meters (2.5 to 3 feet) long and the support members, which lie perpendicular to the longitudinal axis of the spine, are approximately 20.32 to 25.4 centimeters (8 to 10 inches) overall in width, with a recess in the mid-portion of the underside that is about 5.08 centimeters (2 inches) wide and 1.27 centimeters (½ inch) high. The top underpad can be tapered in the direction of the top end of the spine protector to facilitate comfort to the wearer. Both the top and bottom individual support members are equipped with fasteners by which to secure the spine protector into a pouch or vest on the wearer's back. Smaller versions of the protector can be adapted to complement existing equipment such as those used in sports activities.

The top end lower support member may have a flared opening at the top of its aperture to minimize possible pressure points at the lower cervical or upper thoracic areas of and adjacent to the spinal column. The bottom of the lower support at the base of the spine protector may have a tapered shape to better fit to the lower sacral or coccygeal areas of the spinal column.

In an alternative embodiment, where flexibility is not necessary, one portion of the spine protector can be constructed from a single support member with a single underpad of substantially similar size. The size of such a support member can vary and can be molded to be as long and as wide as required to fit over any particular area of the spine where flexure is of no importance.

The bottom or top edge of this one-piece large support member is fastened to the uppermost or lowermost, normal size support member, respectively, in the usual manner.

BRIEF DESCRIPTION OF THE INVENTION

The invention will be more fully described in conjunction with the following drawings wherein:

FIG. 7A is a top view of an alternative component of the invention;

FIG. 7B is a side view of the component shown in FIG. 7A; and

FIG. 7C is an end view of the component shown in FIG. 7B.

DETAILED DESCRIPTION OF THE INVENTION

Figure 1A:
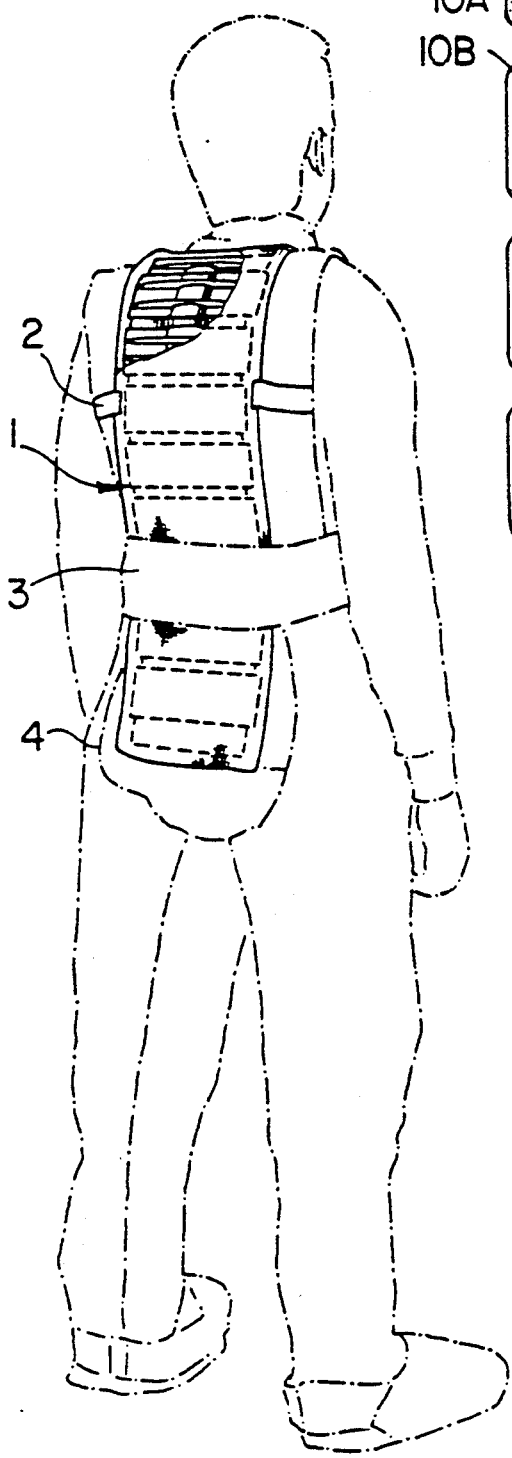
FIG. 1A is a perspective view of a person wearing the spine protector of the present invention when in use with protective clothing, in this example, a bomb suit.

In FIG. 1A, a person is shown wearing the spine protector 1. The spine protector lies with its central portion along the longitudinal axis of the spine. Straps 2 and belts 3 hold the spine protector in place on an underpad 4.

Figure 1B:
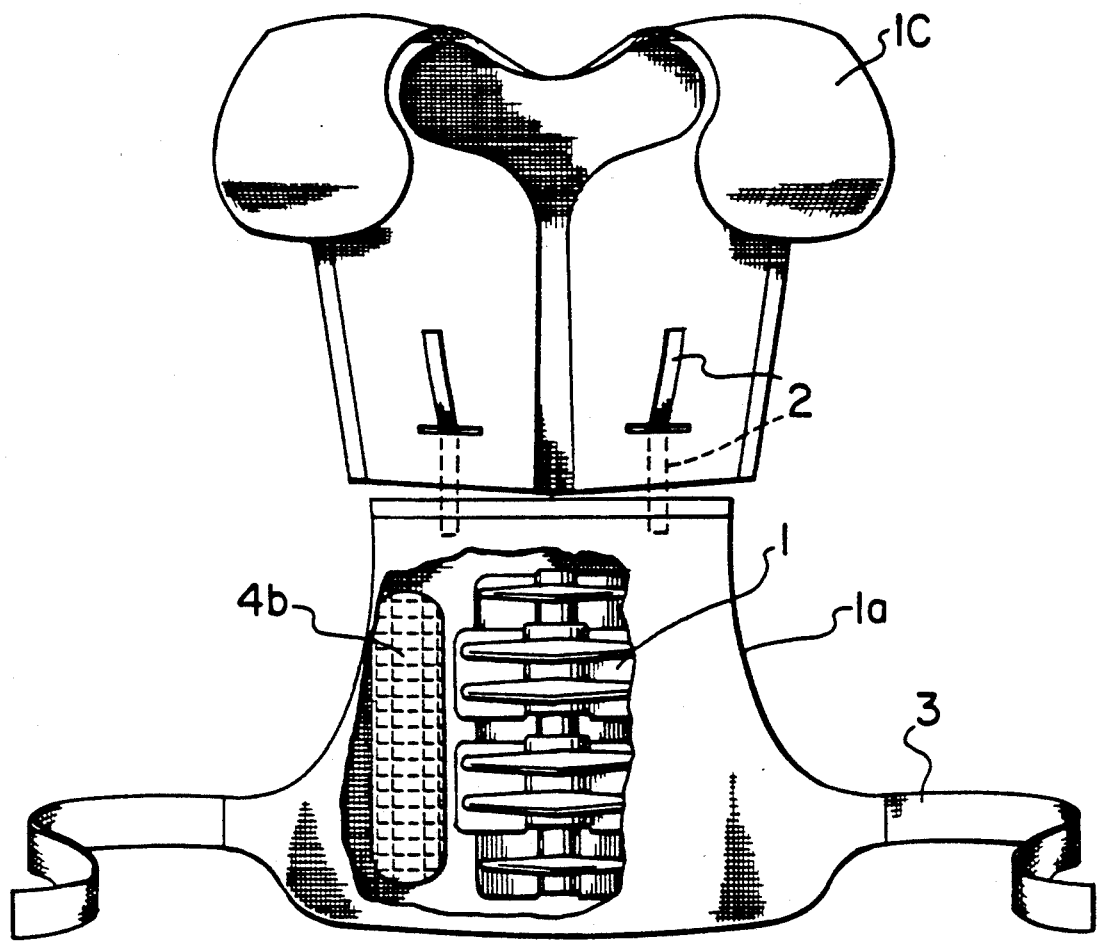
FIG. 1B is a perspective view of the spine protector of the present invention when in use with sports equipment, in this example, a football shoulder pad.

In FIG. 1B, the spine protector lies with its central portion along the longitudinal axis of the spine (not shown) and is mounted within a pouch 1A below a shoulder pad 1C. Straps 2 and belt 3 hold the spine protector pouch 1A in place. Additional padding 4B can be used on each side of the spine protector 1.

Figure 2:
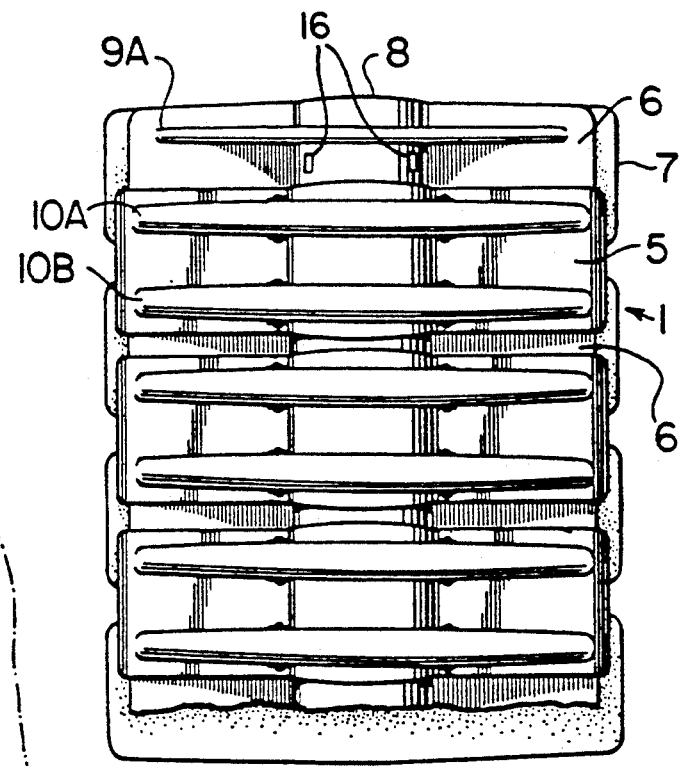
FIG. 2 is a top view of a cut-away portion of a spine protector.

FIG. 2 is a top view of a cut-away portion of the spine protector. The upper elongate rectangular rigid support members 5 overlap rectangular elongate lower rigid support members 6. Curvilinear ribs form part of the upper or outer surface of the support members. The ribs run parallel to the longitudinal axis of the support members, which are, of course, perpendicular to the longitudinal axis of the spine, when in use. In the lower support member 6, rib 9A is shown. In the upper support member 5, ribs 10A and 10B are shown. One also notes that the lower support member 6 sits on an individual underpad 7. These underpads 7 are slightly longer than the lower support members. The underpads are somewhat resilient while the support members are made of a more rigid plastic.

The upper support member 5 is mounted on two lower support members 6 in mating relationship. Rib 10A of upper support member 5 rests on ring 9B (not shown in FIG. 2) of lower support member 6. One also notes concave recesses 8 in the underside of all support members 5, 6. These are more clearly shown in FIG. 4.

Figure 3:
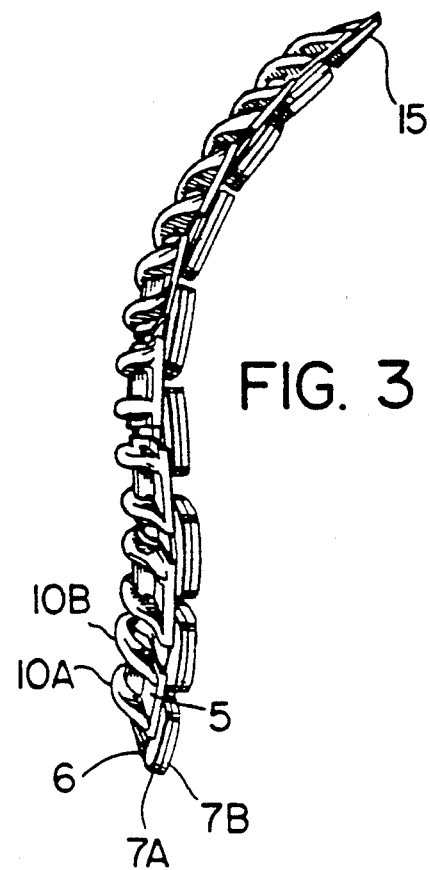
FIG. 3 is a perspective view of the spine protector in a flexed position.

FIG. 3 shows a complete spine protector in a flexed position which can be adjusted to follow the contour of the spinal column. The underpads 7 are comprised of several densities of material in a preferred embodiment. The lowermost material 7A which is in contact with the wearer, is a very resilient low density foam, while the uppermost material 7B is a less resilient, high density foam.

Figure 4:
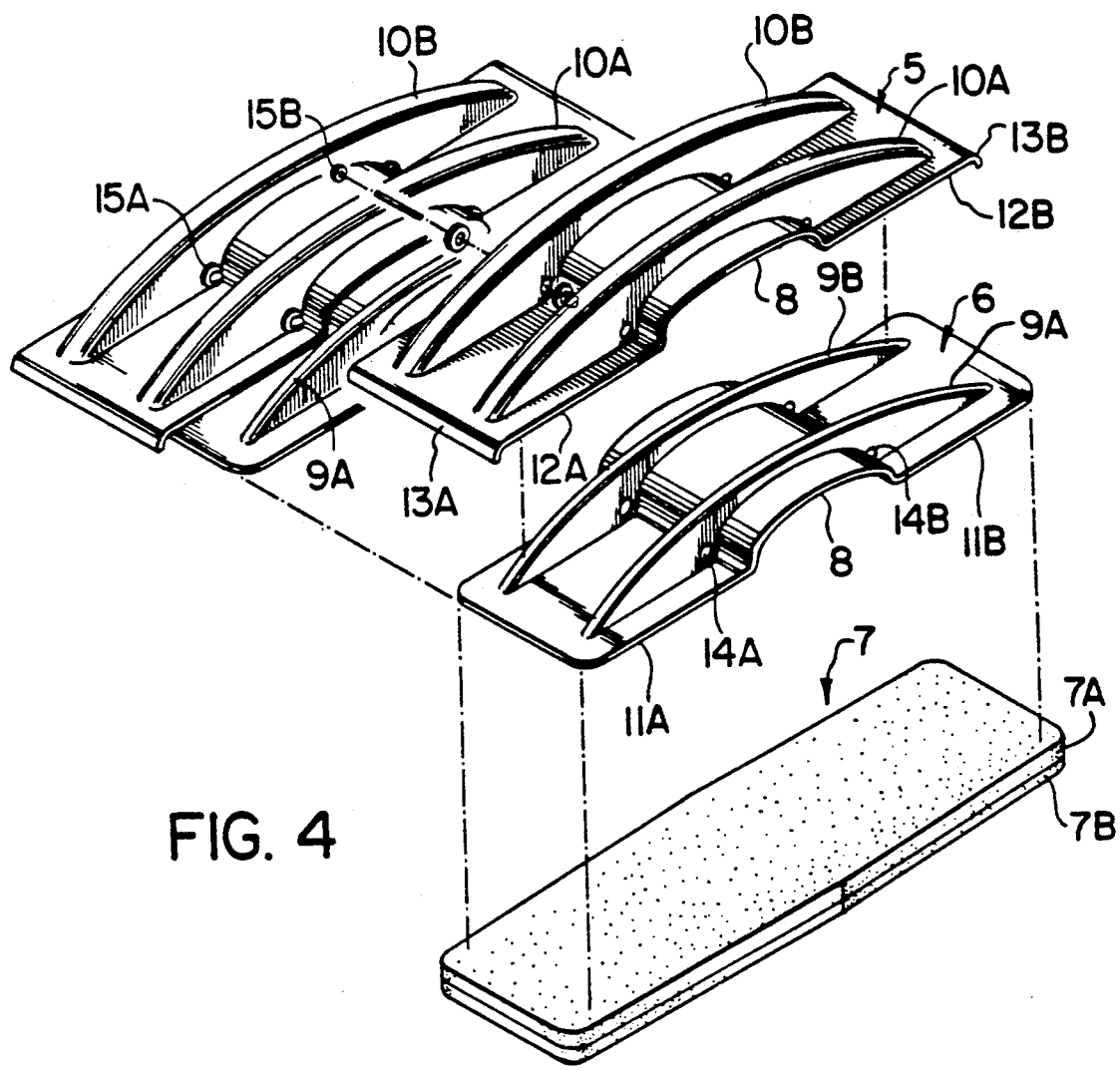
FIG. 4 is an exploded view of the individual components of the invention.

FIG. 4 is an exploded view of the spine protector which clearly shows the overlying relationship of the upper support members 5 and the lower support members 6. The ribs 10A and 10B of the upper support members are wider and longer than the ribs 9A and 9B of the lower support members. There is an overlapping relationship as rib 10A fits matingly upon rib 9B and rib 10B fits matingly upon rib 9A of an adjacent lower support member. In this manner both the upper support members and the lower support members are spaced apart, allowing for greater flexure, while maintaining complete coverage to virtually the entire spinal column.

The concave recess 8 is adapted to be located directly over the vertebrae when the protector is in use. All of the support members 5 and 6, making up the spine protector 1, are formed in this manner. Therefore, when an external force strikes the upper surface of the spine protector, the force is transmitted directly to the substantially planar bottom underside 11A, 11B and 12A, 12B of the support members which are in contact with the spinal structures on either side of the vertebrae. Downwardly turned lips 13A and 13B of the upper support members 5 help keep the lower support members 6 more fully aligned.

Both the upper support members 5 and lower support members 6 are equipped with a pair of aligned apertures 14A, 14B in each of the ribs. When the support members 5 and 6 are placed in an overlapping relationship, the aligned apertures permit a fastener to go through in order to attach the individual components 5 and 6 together. The fasteners are shown as 15A and 15B.

Figure 5:
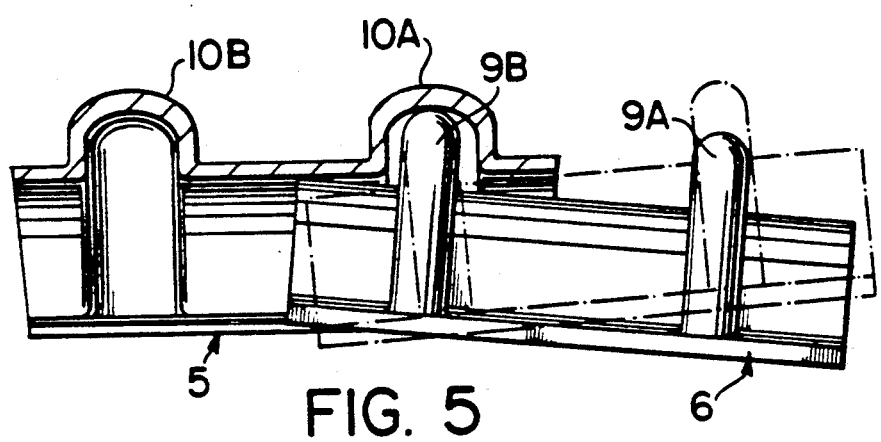
FIG. 5 is a side view of the invention showing its ability to flex.

FIG. 5 is a cut-away section through the longitudinal axis of the spine protector showing rib 10A of the upper member 5 overlapping, in mating relationship, rib 9B of the lower support member 6. The fasteners 15A and 15B are not shown in the drawing. One notes there is sufficient play between rib 9B and rib 10A to make the spine protector flex.

Finally, as shown in FIG. 2, fasteners 16, used to permit a spine protector 1 to be held in place inside a carrying sleeve or vest (not shown), are found on the uppermost and lowermost lower support members 6.

Figure 6:
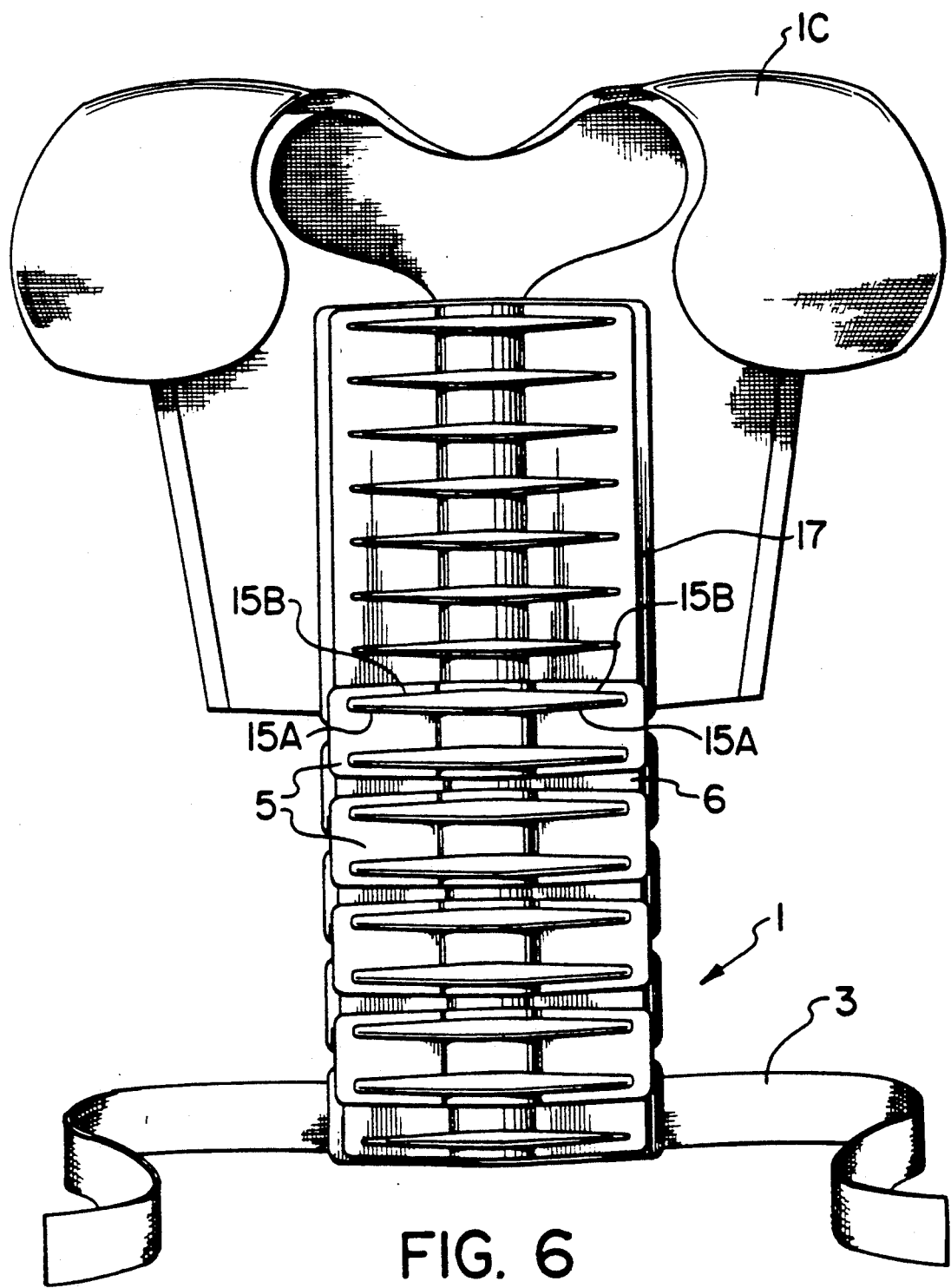
FIG. 6 is a view of an alternative embodiment of the invention.

In an alternative embodiment of the invention as shown in FIG. 6, a non-articulate single piece support member 17 is shown for those applications where flexibility is not required. This support member 17 can be sized to suit the application. A typical application is for use in the upper thoracic and shoulder protection harness used in football or hockey. This support member 17 provides a rigid panel 17 that allows for the simple addition of the lower articulate segments, namely support members 5 and 6, by the normal fastening means and provides a contiguous spine protection assembly.

In FIG. 7A, a non-articulate single piece support member 17 is shown mounted on an underpad 18. On its upper surface 19 are a plurality of reinforcing ribs 20, which in operation, lie perpendicular to the longitudinal axis.

In FIG. 7B, the non-articulate support member 17 is shown from a side view.

FIG. 7C is an end view of support member 17, showing apertures 21, which are adapted to receive fasteners 15A, 15B to connect support member 17 to an upper support member 5.

Although a preferred embodiment of the invention is shown in the drawings, it is understood that any type of spine protector having a concave recess in the mid-portion thereof, and an overlapping relationship with other individual support members, is contemplated by this invention.

What we claim as our invention is:

1. A flexible spine protector for use with protective clothing, sports related activity or any other activity benefiting from spinal protection comprising:

a plurality of elongate substantially rectangular rigid support members and a plurality of resilient elongate substantially rectangular underpads;

said support members being comprised of a plurality of upper support members and lower support members;

each of said upper members being adapted to fit over two adjacent lower support members in mating relationship;

said lower support members being mounted on said underpads;

said underpads and support members being adapted in operation to lie perpendicular to the longitudinal axis of the spine;

said upper support members being spaced apart from adjacent upper support members;

said lower support members mounted on said underpads being space apart from adjacent lower support members mounted on said pads;

said support members being connected to one another in matingly overlapping relationship by a fastening means;

said support members further including a concave central recess on the underside thereof; and said recess being adapted to lie directly over the vertebrae of the wearer, when in use.

2. A spine protector as claimed in claim 1, wherein said support members comprise:

an upper surface which includes at least two curvilinear upwardly projecting ribs which extend along the length of said support members and terminate adjacent the ends thereof;

each of said ribs having its maximum height at the mid-point of said support members.

3. A spine protector as claimed in claim 2, wherein said lower support members include ribs which are shorter in length and narrower in width than said upper support members, such that said ribs of said upper support members overlap said ribs of said lower support members in mating relationship.

4. A spine protector as claimed in claim 3, wherein said fastening means comprises:

a plurality of fasteners;

each of said fasteners passing through at least one rib of said upper support member and one rib of said lower support member in a direction transverse to the longitudinal axis of said ribs.

5. A spine protector as claimed in claim 4, wherein two of said fasteners connect each pair of overlapping ribs of said upper and lower support members.

6. A spine protector as claimed in claim 4, wherein said ribs are loosely connected by said fasteners such that said spine protector is adapted to flex in three dimensions.

7. A spine protector as claimed in claim 1, wherein said upper support members are longer than said lower support members and include on each end thereof, a downwardly projecting lip.

8. A spine protector as claimed in claim 1, wherein a top end and a bottom end lower support member may include fastener apertures by which supporting attachment to a pouch or sleeve can be established.

9. A spine protector as claimed in claim 8, wherein said concave central recess of said top end lower support member is cut-away at its top side to facilitate rearward movement of an occupant's head.

10. A spine protector as claimed in claim 8, wherein said bottom end lower support member is tapered toward the lowermost portion of said spine protector.

11. A spine protector as claimed in claim 1, wherein at least one of said underpads and one of said support members is substantially greater in width than the remainder of said underpads and said support members.

* * * * *